US008110215B2

(12) United States Patent
Koenig et al.

(10) Patent No.: US 8,110,215 B2
(45) Date of Patent: Feb. 7, 2012

(54) PERSONAL CARE PRODUCTS AND METHODS FOR INHIBITING THE ADHERENCE OF FLORA TO SKIN

(75) Inventors: David W. Koenig, Menasha, WI (US); Christine L. Schneider, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1938 days.

(21) Appl. No.: 10/836,449

(22) Filed: Apr. 30, 2004

(65) Prior Publication Data
US 2005/0244481 A1    Nov. 3, 2005

(51) Int. Cl.
*A61F 13/00* (2006.01)
(52) U.S. Cl. .......................... 424/443; 424/400
(58) Field of Classification Search ............ None
See application file for complete search history.

(56) References Cited

U.S. PATENT DOCUMENTS

| | | | |
|---|---|---|---|
| 4,100,324 | A | 7/1978 | Anderson et al. |
| 4,255,337 | A | 3/1981 | Kaiser et al. |
| 4,798,603 | A | 1/1989 | Meyer et al. |
| 4,820,447 | A * | 4/1989 | Medcalf et al. ............ 510/151 |
| 4,855,137 | A | 8/1989 | Keri et al. |
| 4,904,524 | A * | 2/1990 | Yoh ................... 442/61 |
| 5,176,668 | A | 1/1993 | Bernardin |
| 5,176,672 | A | 1/1993 | Bruemmer et al. |
| 5,192,606 | A | 3/1993 | Proxmire et al. |
| 5,509,915 | A | 4/1996 | Hanson et al. |
| 5,518,733 | A | 5/1996 | Lamothe et al. |
| 5,587,358 | A | 12/1996 | Sukigara et al. |
| 5,604,262 | A | 2/1997 | Wood |
| 5,656,278 | A | 8/1997 | Enjolras |
| 5,683,991 | A | 11/1997 | Guggenbichler et al. |
| 5,718,694 | A | 2/1998 | Rupp |
| 5,843,056 | A | 12/1998 | Good et al. |
| 5,855,999 | A | 1/1999 | McCormack |
| 5,879,341 | A | 3/1999 | Odorzynski et al. |
| 5,891,833 | A * | 4/1999 | Wei et al. ................ 510/121 |
| 5,962,517 | A | 10/1999 | Murad |
| 6,028,018 | A | 2/2000 | Amundson et al. |
| 6,217,852 | B1 * | 4/2001 | Gildenberg et al. ............ 424/59 |
| 6,497,862 | B2 * | 12/2002 | Oku et al. ................ 424/65 |
| 6,562,770 | B2 | 5/2003 | Pashkovski et al. |
| 6,586,023 | B1 * | 7/2003 | Song et al. ............ 426/5 |
| 2005/0148490 | A1 | 7/2005 | Krzysik et al. |
| 2005/0239669 | A1 | 10/2005 | Krzysik et al. |

FOREIGN PATENT DOCUMENTS

CN          1112438          11/1995
(Continued)

OTHER PUBLICATIONS

Franck et al., Inulin, Feb. 2002, Ghent, Belgium, and Munster, pp. 439-448.*

(Continued)

*Primary Examiner* — Anand Desai
*Assistant Examiner* — Melissa Mercier
(74) *Attorney, Agent, or Firm* — Armstrong Teasdale LLP

(57) ABSTRACT

The present invention relates to methods and personal care products, such as wipes and absorbent articles, capable of providing a skin health benefit when used in the intended fashion. More specifically, the products described herein comprise at least one fructose polymer capable of inhibiting the adherence of flora to surfaces, such as skin, mucosa, or inanimate surfaces.

11 Claims, 2 Drawing Sheets

FOREIGN PATENT DOCUMENTS

| | | |
|---|---|---|
| CN | 1176109 | 3/1998 |
| CN | 1216252 | 5/1999 |
| CN | 1346663 | 5/2002 |
| JP | 05-097626 | 4/1993 |
| JP | 10-072312 | 3/1998 |
| JP | 2000-178175 | 6/2000 |
| RU | 2138247 | 9/1999 |
| RU | 2162684 | 2/2001 |
| WO | WO 96/23479 A2 | 8/1996 |
| WO | WO 97/29763 A1 | 8/1997 |
| WO | 9813467 A1 | 4/1998 |
| WO | WO 98/44901 A1 | 10/1998 |
| WO | WO 98/44926 A1 | 10/1998 |
| WO | WO 98/47374 A1 | 10/1998 |
| WO | WO 99/66796 A1 | 12/1999 |
| WO | WO 00/61201 A1 | 10/2000 |
| WO | WO 02/055053 | 7/2002 |

OTHER PUBLICATIONS

Franck et al. Polysaccharides and polyamides in the food industry: Properties, Production, and Patents, Jun. 2005, chapter 14.*

Calderone et al., "Adherence and Receptor Relationships of *Candida albicans*", Microbiological Reviews, 1991, 55(1): 1-20.

Hostetter, "Adhesins and Ligands Involved in the Interaction of *Candida* spp. with Epithelial and Endothelial Surfaces", Clinical Microbiology Reviews, 1994, 7(1): 29-42.

Layne et al, "The Dephosphorylation of Phosphoglucomutase by Nucleophilic Reagents", Journal of Biological Chemistry, 1975, 250: 966-72.

Melese et al, "Pancreatic epithelium is permeable to sucrose and inulin across secretory cells", Proceedings of the National Academy of Sciences, USA, 1983, 80: 4870-4874.

Praznick et al, "Application of Gel Permeation Chromatographic Systems to the Determination of the Molecular Weight of Inulin", Journal of Chromatography, 1985, 348:187-197.

Roberfroid, "Dietary Fiber, Inulin, and Oligofructose: a Review Comparing their Physiological Effects", Critical Reviews in Food Science and Nutrition, 1993, 33(2): 103-148.

Tronchin et al, "Fungal Cell Adhesion Molecules in *Candida albicans*", European Journal of Epidemiology, 1991, 7(1): 23-33.

International Search Report and Written Opinion from PCT/US2005/008536, dated Jul. 22, 2005.

* cited by examiner

PERSONAL CARE PRODUCTS AND METHODS FOR INHIBITING THE ADHERENCE OF FLORA TO SKIN

BACKGROUND OF INVENTION

The present invention relates to personal care products, such as wipes and absorbent articles, that are capable of providing a skin health benefit to the user. More particularly, the present invention relates to wipes and absorbent articles comprising at least one fructose polymer that inhibits the adherence of flora to skin or mucosa.

A variety of flora may be found on the surface of skin at any given time. The adherence to the skin of problem flora, such as pathogenic bacteria and yeast, has been associated with numerous ailments, including skin infections, diaper rash, urinary or vaginal infections, and malodors. Various products are commercially available to clean the surface of skin and to remove problem flora therefrom. For example, wet wipes are commonly used to remove excrement and flora from the skin of babies. These wet wipes typically comprise a surfactant system for cleaning the skin and removing waste located thereon. In some cases, wet wipes may comprise an antibacterial agent, such as an organic acid, which can be used in combination with the surfactant to kill bacteria located on the skin's surface.

Also, various antibacterial soaps and cleansers are available to cleanse hands and kill flora adhered to the skin's surface. These antibacterial soaps are generally highly effective in killing bacteria located on the skin.

Although various products such as wet wipes and soaps are available to clean and sanitize skin, these products can sometimes be harsh on the skin after repeated use. In some cases, skin can become dry or chaffed, and the use of the sanitizing product must be discontinued until the skin heals. As such, it would be desirable to provide products, such as wet wipes, that could not only clean skin, but also keep bacteria from adhering thereto and remaining on the skin.

SUMMARY OF THE INVENTION

The present invention relates to personal care products and methods for inhibiting the adherence of flora to the skin. More specifically, the present invention relates to products such as wet wipes or absorbent articles comprising fructose polymers, which act to inhibit the adherence of flora to the surface of skin or mucosa.

In one aspect, the present invention provides a wipe, such as a wet wipe, comprising a fibrous sheet material and a liquid formulation. The liquid formulation preferably comprises at least about 0.1% (by total weight of the liquid formulation) of a fructose polymer. The wipe may also be a dry wipe.

Also provided is an abosrbent article. The absorbent article comprises a substrate and a formulation. Preferably, the formulation comprises at least about 0.1% (by weight of the formulation of a fructose polymer.

The wipes and absorbent articles described herein may also be used in a method for inhibiting the adherence of flora to a surface, such as skin, mucosa, or inanimate surfaces. For example, in one aspect, the method comprises contacting a wet wipe with the surface, the wet wipe comrpising a fibrous sheet material and a liquid formulation, and transferring the liquid formulation to the surface. Preferably the liquid formulation comprises at least about 0.1% (by total weight of the liquid formulation) of a fructose polymer.

DETAILED DESCRIPTION OF THE PREFERRED EMBODIMENTS

Figure 1:
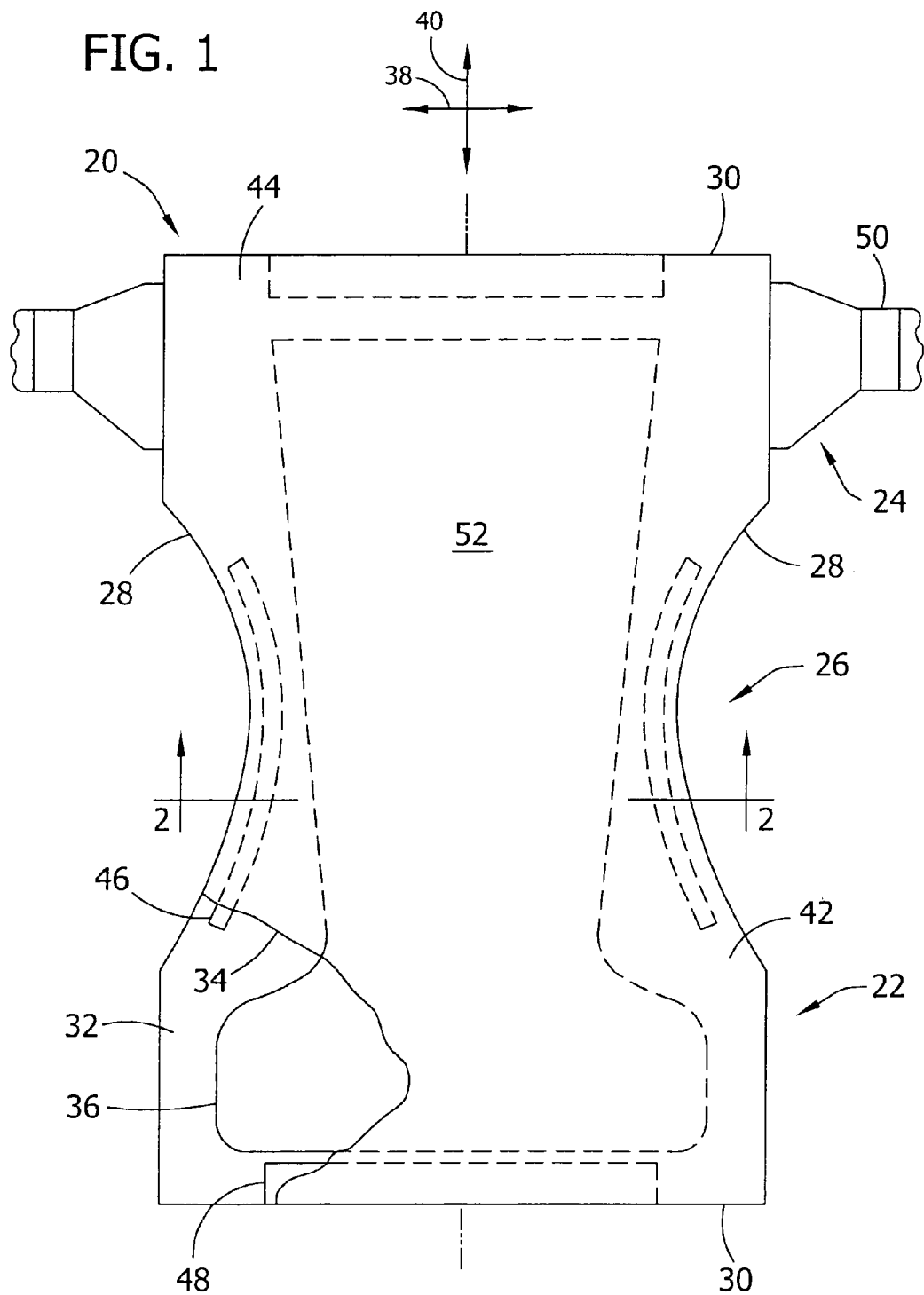
FIG. 1 representatively shows a partially cut away top plan view of an absorbent article in a stretched and laid flat condition with the surface of the article which contacts the skin of the wearer facing the viewer.

In accordance with the present invention, it has been discovered that certain carbohydrates, such as fructose polymers, can be utilized in combination with personal care products, such as wipes or absorbent articles, to impart a skin health benefit by inhibiting the adherence of flora to the surface of skin or mucosa. By introducing a fructose polymer, or a combination of fructose polymers, into a formulation that is used in combination with a wipe or absorbent article substrate, it is possible to transfer the fructose polymer to the skin during use of the product and to inhibit the adherence of various bacteria and/or yeast to the skin. This technology can be used to reduce skin infections and treat wounds, as well as treat skin, such that it will stay clean and hygenic.

Although discussed primarily in terms of use with skin and mucosa, the products (and methods) described herein are also suitable for use on non-skin, inanimate surfaces (e.g., hard surfaces). Examples of such hard surfaces include wood, countertops, stainless steel, etc. For example, by contacting a wipe comprising a fructose polymer with the inanimate surface, it is possible to transfer the fructose polymer to the surface and inhibit the adherence of various flora to the surface, thus enhancing the surface's cleanliness.

The personal care products of the present invention include at least one fructose polymer. As used herein, the term "fructose polymer" is meant to include fructans such as inulin, levan, or graminan, with a degree of polymerization of greater than two. In general, graminan, levan, and inulin differ in the amount of branching that is present in their fructose chains and in the types of bonds connecting the individual fructose units. For example, levans generally consist of chains of fructose units that are typically connected by a $\beta(2\text{-}6)$ bond. Although levans may occur as linear chain carbohydrates, they are more typically composed of branched fructose chains. In contrast, inulins generally consist of linear chains of fructose units that are typically connected by $\beta(2\text{-}1)$ linkages. Graminans, or mixed type fructans, may comprise both $\beta(2\text{-}1)$ and $\beta(2\text{-}6)$ linkage bonds between fructose units. Regardless, fructans in general are suitable for use in the present invention.

Inulin may be found widely distributed in nature. For example, inulin may be found as a plant storage carbohydrate, and is common to plants of the Composite family. Inulin may be derived from a variety of plants, such as Jerusalem artichoke and Dahlia tuber, and is a major constituent of some herbs, such as burdock root, dandelion root, elecampane root, chicory root, and codonopsis, among others. Inulin may comprise fructose polymers of varying chain lengths, depending on the source from which the inulin is derived. For example, inulin derived from plants typically has a degree of polymerization of from about 2 to about 100 or more fructose units, while inulin derived from a bacterial origin may have an even higher degree of polymerization.

The terms "fructooligosaccharide" or "oligofructose," used interchangeably herein, are meant to refer to fructose polymers with a lower degree of polymerization, for example, between about 2 and about 20. The fructose polymers described herein are capable of improving the health of skin contacted by the wipe or absorbent article, comprising the fructose polymer, during normal use by inhibiting the adherence of flora to the skin. Numerous personal care products can be used in combination with the fructose polymers described herein in accordance with the present invention to impart a skin health benefit to the user. For example, one or more of the fructose polymers described herein can be used in combination with wipes, such as wet wipes, hand wipes, face wipes, cosmetic wipes, household wipes, industrial wipes, dry wipes, feminine wipes, and the like, to inhibit the attachment of flora to the surface of skin, mucosa, or inanimate surfaces such as wood, countertops, stainless steel, etc.

In addition, the fructose polymers described herein can be used in combination with absorbent articles such as diapers, training pants, adult incontinence garments, feminine napkins, tampons, interlabial pads, facial tissue, wound management products, paper towels, bath tissue, and the like. As will be understood by one skilled in the art, the fructose polymers may be directly impregnated on the wipe or absorbent substrate, or may be in a liquid formulation or ointment used with the wipe or absorbent article.

Although discussed primarily in combination with a wipe substrate, it should be understood that the fructose polymers can also be used in combination with other numerous absorbent products as noted above. Materials suitable for use as the substrate of the wipe are well known to those skilled in the art, and typically include a fibrous sheet material, which may be either woven or nonwoven. For example, the wipe substrate incorporating the fructose polymers described herein to improve skin health may include nonwoven fibrous sheet materials, which include meltblown, coform, air-laid, bonded-carded web materials, hydroentangled materials, and combinations thereof. Such materials can be comprised of synthetic or natural fibers, or a combination thereof. Typically, wipes define a basis weight of from about 25 to about 120 grams per square meter and desirably from about 40 to about 90 grams per square meter.

In a particular embodiment, the wipes incorporating the fructose polymers described herein comprise a coform basesheet of polymeric microfibers and cellulosic fibers having a basis weight of from about 60 to about 80 grams per square meter and desirably about 75 grams per square meter. Such coform basesheets are manufactured generally as described in U.S. Pat. No. 4,100,324, which is incorporated by reference. Typically, such coform basesheets comprise a gas-formed matrix of thermoplastic polymeric meltblown microfibers, such as, for example, polypropylene microfibers, and cellulosic fibers, such as, for example, wood pulp fibers.

The relative percentages of the polymeric microfibers and cellulosic fibers in the coform basesheet can vary over a wide range depending upon the desired characteristics of the wet wipes. For example, the coform basesheet may comprise from about 20 to about 100 weight percent, desirably from about 20 to about 60 weight percent, and more desirably from about 30 to about 40 weight percent of the polymeric microfibers based on the dry weight of the coform basesheet being used to provide the wipes.

Alternatively, the wipes incorporating the fructose polymers described herein can comprise a composite, which includes multiple layers of materials such as those described in U.S. Pat. No. 6,028,018, which is incorporated by reference. For example, the wipes may include a three layer composite, which includes an elastomeric film or meltblown layer between two coform layers as described above. In such a configuration, the coform layers may define a basis weight of from about 15 to about 30 grams per square meter and the elastomeric layer may include a film material such as a polyethylene metallocene film.

As mentioned above, one type of wipe suitable for use in combination with the fructose polymers is a wet wipe. In addition to the wipe substrate, wet wipes also comprise a liquid solution or formulation. The liquid solution or formulation can be any liquid, which can be absorbed into the wet wipe basesheet and may include any suitable components, which provide the desired wiping properties. For example, the components may include water, emollients, surfactants, fragrances, preservatives, organic or inorganic acids, chelating agents, pH buffers, or combinations thereof as are well known to those skilled in the art. Further, the liquid may also contain lotions, medicaments, and/or antimicrobials.

As previously mentioned, the wet wipe may contain fructose polymers which are absorbed into the wet wipes and/or present in the wet wipe solution. The amount of liquid contained within each wet wipe may vary depending upon the type of material being used to provide the wet wipe, the type of liquid being used, the type of container being used to store the wet wipes, and the desired end use of the wet wipe. Generally, each wet wipe can contain from about 150 to about 600 weight percent and desirably from about 250 to about 450 weight percent liquid based on the dry weight of the wipe for improved wiping. In a particular aspect, the amount of liquid contained within the wet wipe is from about 300 to about 400 weight percent and desirably about 330 weight percent based on the dry weight of the wet wipe. If the amount of liquid is less than the above-identified ranges, the wet wipe may be too dry and may not adequately perform. If the amount of liquid is greater than the above-identified ranges, the wet wipe may be oversaturated and soggy and the liquid may pool in the bottom of the container holding the wet wipes.

Each wet wipe is generally rectangular in shape and may have any suitable unfolded width and length. For example, the wet wipe may have an unfolded length of from about 2.0 to about 80.0 centimeters and desirably from about 10.0 to about 25.0 centimeters and an unfolded width of from about 2.0 to about 80.0 centimeters and desirably from about 10.0 to about 25.0 centimeters. Typically, each individual wet wipe is arranged in a folded configuration and stacked one on top of the other to provide a stack of wet wipes. Such folded configurations are well known to those skilled in the art and include c-folded, z-folded, quarter-folded configurations and the like. The stack of folded wet wipes may be placed in the interior of a container, such as a plastic tub, to provide a package of wet wipes for eventual sale to the consumer. Alternatively, the wet wipes may include a continuous strip of material which has perforations between each wipe and which may be arranged in a stack or wound into a roll for dispensing.

The fructose polymers described herein may further be incorporated into an absorbent article. As used herein, the phrase "absorbent article" generally refers to devices which absorb and contain body fluids, and more specifically, refers to devices which are placed against or near the skin to absorb and contain the various fluids dischargd from the body. Although described in detail in relation to a disposable diaper, it will be understood that the fructose polymers described herein may also be used in combination with other absorbent articles, such as training pants, adult incontinence garments, feminine napkins, panty liners, tampons, interlabial pads, facial tissue, paper towels, bath tissue, and wound management products, wherein the inhibition of the adherence of flora to skin or mucosa would be beneficial.

Figure 2:
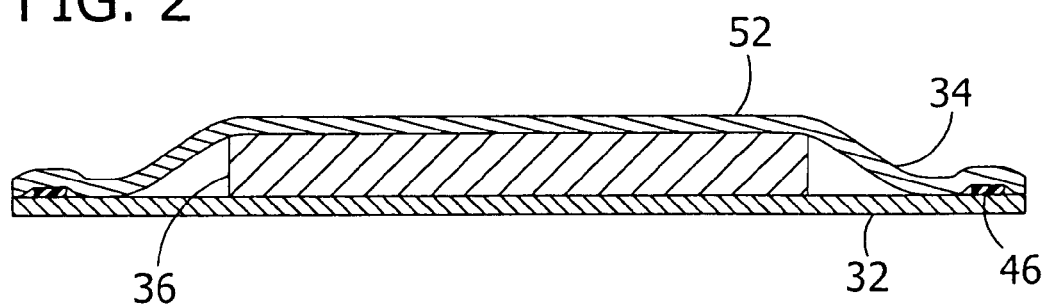
FIG. 2 representatively shows a sectional view of the absorbent article of FIG. 1 taken along line 2-2.

With reference to FIGS. 1 and 2, an integral absorbent garment article, such as a disposable diaper 20, generally defines a front waist section 22, a rear waist section 24, an intermediate section 26 which interconnects the front and rear waist section, a pair of laterally opposed side edges 28, and a pair of longitudinally opposed end edges 30. The front and rear waist sections include the general portions of the article which are constructed to extend substantially over the wearer's front and rear abdominal regions, respectively, during use. The intermediate section of the article includes the general portion of the article which is constructed to extend through the wearer's crotch region between the legs. The opposed side edges 28 define leg openings for the diaper and generally are curvilinear or contoured to more closely fit the legs of the wearer. The opposed end edges 30 define a waist opening for the diaper 20 and typically are straight but may also be curvilinear.

FIG. 1 is a representative plan view of the diaper 20 in a flat, non-contracted state. Portions of the structure are partially cut away to more clearly show the interior construction of the diaper 20, and the surface of the diaper which contacts the wearer is facing the viewer. The diaper 20 includes a substantially liquid impermeable outer cover 32, a porous, liquid permeable bodyside liner 34 positioned in facing relation with the outer cover 32, and an absorbent body 36, such as an absorbent pad, which is located between the outer cover and the bodyside liner. The diaper 20 also defines a lateral direction 38 and a longitudinal direction 40. Marginal portions of the diaper 20, such as marginal sections of the outer cover 32, may extend past the terminal edges of the absorbent body 36. In the illustrated embodiment, for example, the outer cover 32 extends outwardly beyond the terminal marginal edges of the absorbent body 36 to form side margins 42 and end margins 44 of the diaper 20. The bodyside liner 34 is generally coextensive with the outer cover 32, but may optionally cover an area which is larger or smaller than the area of the outer cover 32, as desired.

To provide improved fit and to help reduce leakage of body exudates from the diaper 20, the side margins 42 and end margins 44 of the diaper may be elasticized with suitable elastic members, such as leg elastic members 46 and waist elastic members 48. For example, the leg elastic members 46 may include single or multiple strands of elastic or elastomeric composites which are constructed to operably gather and shirr the side margins 42 of the diaper 20 to provide elasticized leg bands which can closely fit around the legs of the wearer to reduce leakage and provide improved comfort and appearance. Similarly, the waist elastic members 48 can be employed to elasticize the end margins 44 of the diaper 20 to provide elasticized waistbands. The waist elastics are configured to operably gather and shirr the waistband sections to provide a resilient, comfortably close fit around the waist of the wearer.

The elastic members 46 and 48 are secured to the diaper 20 in an elastically contractible condition so that in a normal under strain configuration, the elastic members effectively contract against the diaper 20. For example, the elastic members 46 and 48 may be elongated and secured to the diaper 20 while the diaper is in an uncontracted condition. In FIGS. 1 and 2, the elastic members 46 and 48 are illustrated in their uncontracted, stretched condition for the purpose of clarity. The diaper 20 may also include a pair of elasticized, longitudinally extending containment flaps (not shown), which are configured to maintain an upright, perpendicular arrangement in at least the intermediate section 26 of the diaper 20 to serve as an additional barrier to the lateral flow of body exudates. Suitable constructions and arrangements of containment flaps are well known to those skilled in the art.

Alternatively, the diaper 20 may include a pair of separate, elasticized and gathered leg gussets (not shown) or combination leg gussets/containment flaps (not shown) which are attached to the diaper along the side margins 42 in at least the intermediate section 26 of the diaper 20 to provide elasticized leg cuffs. Such gussets or combination gussets/containment flaps may be configured to extend beyond and bridge across the respective concave portion of the side margins 42.

The diaper 20, as representatively illustrated in FIGS. 1 and 2, may further include a pair of fasteners 50 employed to secure the diaper 20 about the waist of a wearer. Suitable fasteners 50 include hook-and-loop type fasteners, adhesive tape fasteners, buttons, pins, snaps, mushroom-and-loop fasteners, and the like. A cooperating side panel member can be associated with each fastener and may be constructed to be nonelasticized, or to be elastically stretchable at least along the lateral direction 38 of diaper 20.

The diaper may further include a surge management layer (not shown) positioned between the bodyside liner 34 and the absorbent body 36 which is configured to efficiently hold and distribute liquid exudates to the absorbent body 36. The surge management layer can prevent the liquid exudates from pooling and collecting on the portion of the diaper positioned against the wearer's skin, thereby reducing the level of skin hydration. Suitable constructions and arrangements of surge management layers are well known to those skilled in the art. Other suitable diaper components may also be incorporated on absorbent articles described herein.

The diaper 20 may be of various suitable shapes. For example, the diaper may have an overall rectangular shape, T-shape, or an approximately hour-glass shape. In the shown embodiment, the diaper 20 is I-shaped. Examples of diaper configurations suitable for use in connection with the instant application and other diaper components suitable for use on diapers are described in U.S. Pat. No. 4,798,603 issued Jan. 17, 1989 to Meyer et al.; U.S. Pat. No. 5,176,668 issued Jan. 5, 1993, to Bernardin; U.S. Pat. No. 5,176,672 issued Jan. 5, 1993 to Bruemmer et al.; U.S. Pat. No. 5,192,606 issued Mar. 9, 1993 to Proxmire et al.; and U.S. Pat. No. 5,509,915 issued Apr. 23, 1996 to Hanson et al., the disclosures of which are hereby incorporated by reference. The various aspects and configuration of the invention can provide distinctive combinations of softness, body conformity, reduced red-marking of the wearer's skin, reduced hydration, and improved containment of body exudates.

The various components of the diaper 20 are integrally assembled together employing various types of suitable attachment means, such as adhesive, sonic bonds, thermal bonds, or combinations thereof. In the shown embodiment, for example, the bodyside liner 34 and the outer cover 32 are assembled to each other and to the absorbent body 36 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 46 and 48 and the fasteners 50, may be assembled into the diaper 20 by employing the above-identified attachment mechanisms.

The outer cover 32 of the diaper 20, as representatively illustrated in FIGS. 1 and 2, may suitably be composed of material which is either liquid permeable or liquid impermeable. It is generally preferred that the outer cover 32 be formed from a material which is substantially impermeable to liquids. For example, a typical outer cover can be manufactured from a thin plastic film or other flexible liquid-impermeable material. For example, the outer cover 32 may be formed from a polyethylene film having a thickness of from about 0.012 millimeter (0.5 mil) to about 0.051 millimeter (2.0 mils). If it is desired to present the outer cover with a more clothlike feeling, the outer cover 32 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mils) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). Methods of forming such clothlike outer covers are known to those skilled in the art. Further, the outer cover 32 may be formed of a woven or nonwoven fibrous web layer which has been totally or partially constructed or treated to impart a desired level of liquid impermeability to selected regions that are adjacent or proximate to the absorbent body 36.

Desirably, the outer cover 32 may be composed of a "breathable" material which permits vapors to escape from the absorbent body 36 while still preventing liquid exudates from passing through the outer cover 32. For example, the outer cover 32 is desirably constructed to be permeable to at least water vapor and has a water vapor transmission rate of at least about 1000 g/m²/24 hours, desirably at least about 1500 g/m²/24 hours, more desirably at least about 2000 g/m²/24 hours, and even more desirably at least about 3000 g/m²/24 hours. Materials which have a water vapor transmission rate less than those above do not allow a sufficient amount of air exchange and undesirably result in increased levels of skin hydration. As used herein, the phrase "water vapor transmission rate" (WVTR) refers to the WVTR value according to the Water Vapor Transmission Rate Test which is described in further detail herein below.

In a particular embodiment, the outer cover 32 is provided by a microporous film/nonwoven laminate material comprising a spunbond nonwoven material laminated to a microporous film. For example, the laminate may include a 0.6 osy (20.4 gsm) polypropylene spunbond material thermally attached to a 18.7 gsm stretched microporous film. The film may include from about 20 percent to about 75 percent by weight calcium carbonate particulates and the remainder primarily low density polyethylene. The film is then stretched which causes the polyethylene component to stretch while the particulates remain unstretched, thus causing voids to develop around the calcium carbonate particles in the film. The resulting laminate may define a water vapor transmission rate of from about 1000 to about 5000 g/m²/24 hours.

Examples of suitable breathable materials for the outer cover 32 are also described in U.S. Pat. No. 5,879,341 issued Mar. 9, 1999 to Odorzynski et al. and entitled "ABSORBENT ARTICLE HAVING A BREATHABILITY GRADIENT"; U.S. Pat. No. 5,843,056 issued Dec. 1, 1988, to Good et al. and entitled ABSORBENT ARTICLE HAVING A COMOSITE BREATHABLE OUTER COVER"; and U.S. Pat. No. 5,855,999 issued Jan. 5, 1999 to McCormack et al. and entitled "BREATHABLE, CLOTH-LIKE FILM/NON-WOVEN COMPOSITE", the disclosures of which are herein incorporated by reference.

The absorbent body 36 of the diaper 20, as representatively illustrated in FIGS. 1 and 2, may suitably comprise a matrix of hydrophilic fibers, such as a web of cellulosic fluff, mixed with particles of a high-absorbency material commonly known as superabsorbent material. In a particular embodiment, the absorbent body 36 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent body 36 to better contain and absorb body exudates. The concentration of the superabsorbent particles may also vary through the thickness of the absorbent body 36. Alternatively, the absorbent body 36 may comprise a laminate of fibrous webs and superabsorbent material or other suitable means of maintaining a superabsorbent material in a localized area.

The absorbent body 36 may have any of a number of shapes. For example, the absorbent core may be rectangular, I-shaped, or T-shaped. It is generally preferred that the absorbent body 36 be narrower in the crotch area than in the front or rear portions of the diaper 20. The size and the absorbent capacity of the absorbent body 36 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va., and DOW DRYTECH 2035LD polymer available from Dow Chemical Company located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on a total weight of the absorbent body 36.

Optionally, a substantially hydrophilic tissue wrapsheet (not shown) may be employed to help maintain the integrity of the airlaid fibrous structure of the absorbent body 36. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer, which helps to rapidly distribute liquid over the mass of absorbent fibers comprising the absorbent body. In another aspect of the invention, the wrapsheet material on one side of the absorbent fibrous mass may be bonded to the wrapsheet located on the opposite side of the fibrous mass.

The bodyside liner 34, as representatively illustrated in FIGS. 1 and 2, suitably presents a bodyfacing surface, 52, which is compliant, soft feeling, and non-irritating to the wearer's skin. Further, the bodyside liner 34 may be less hydrophilic than the absorbent body 36, to present a relatively dry surface to the wearer, and may be sufficiently porous to be liquid permeable, permitting liquid to readily penetrate through its thickness. A suitable bodyside liner 34 may be manufactured from a wide selection of web materials, such as porous foams, reticulated foams, apertured plastic films, natural fibers (i.e., wood or cotton fibers), synthetic fibers (i.e., polyester or polypropylene fibers), or a combination of natural and synthetic fibers. The bodyside liner 34 is suitably employed to help isolate the wearer's skin from liquids held in the absorbent body 36.

Various woven and nonwoven fabrics can be used for the bodyside liner 34. For example, the bodyside liner 34 may be composed of a meltblown or spunbonded web of polyolefin fibers. The bodyside liner 34 may also be a bonded-carded web composed of natural and/or synthetic fibers. The bodyside liner 34 may be composed of a substantially hydrophobic material, and the hydrophobic material may, optionally, be treated with a surfactant, a wetting agent, or otherwise processed to impart a desired level of wettability and hydrophilicity.

In a particular embodiment, the bodyside liner 34 comprises a nonwoven, spunbond, polypropylene fabric composed of about 2.8-3.2 denier fibers formed into a web having a basis weight of about 20 grams per square meter and a density of about 0.13 gram per cubic centimeter. The fabric may be surface treated with about 0.3 weight percent of a surfactant mixture, which contains a mixture of AHCOVEL Base N-62 and GLUCOPOAN 220UP surfactant in a 3:1 ratio based on a total weight of the surfactant mixture. The ANCOVEL Base N-62 is purchased from Hodgson Textile Chemicals Inc., (Mount Holly, N.C.) and includes a blend of hydrogenated ethoxylated castor oil and sorbitan monooleate in a 55:45 weight ratio. The GLUCOPAN 220UP is purchased from Henkel Corporation and includes alkyl polyglycoside. The surfactant may be applied by any conventional means, such as spraying, printing, brush coating, or the like. The surfactant may be applied to the entire bodyside liner 34, or may be selectively applied to particular sections of the bodyside liner 34, such as the medial section along the longitudinal centerline of the diaper, to provide greater wettability of such sections.

One or more fructose polymers may be introduced into or onto a fibrous wipe substrate, an absorbent substrate, or a solution or ointment for use with a wipe substrate or absorbent article. Without being bound to any particular theory, it is believed that when the product comprising the fructose polymer contacts a surface, the fructose polymers also contact the surface and are actually transferred to the surface, thereby inhibiting the adherence of flora thereto. This mechanism may be a type of displacement mechanism by which the fructose polymers attach to the surface. Alternatively, when the product contacts the surface, the fructose polymers may come in contact with flora and coat the flora, and thereby inhibit the adherence of flora to the portion of the surface contacted by the product.

The fructose polymers present in or on the product preferably inhibit the adherence of at least one type of flora to the surface of skin, mucosa, or an inanimate surface. As noted above, flora are often naturally found on the skin or mucosal surfaces of the body. In particular, problem flora, such as pathogenic bacteria or yeast, are associated with numerous ailments, including skin infections, diaper rash, urinary or vaginal infections, and malodors, among others. It is thus often desirable to inhibit the adherence of such flora to the surface of skin or mucosa. Problem flora may include a variety of microorganisms, such as Gram negative bacteria, Gram positive bacteria, acid fast bacteria, *Mycoplasma*, fungi, yeast, and viruses. Some specific examples of problem flora include *Candida albicans, Proteus mirabilis*, and *Pseudomonas aeruginosa*, among others. Another flora, *Staphylococcus epidermidis*, may become an opportunistic pathogen by spreading into the blood through breaks in skin barriers. It will be apparent to those skilled in the art that there are numerous other examples of flora, other than those described herein, for which it may be desirable to inhibit the adherence, and that the adherence of these flora may be controlled in a manner similar to that described herein.

The fructose polymers for use in combination with the products described herein comprise fructose units linked to form a carbohydrate chain. Suitable examples of fructose polymers include fructans such as inulin, levan, and graminan. The source of the fructose polymers is not critical. For example, inulin is a common plant storage carbohydrate for the Composite family, and may be derived from a variety of plants and herbs. More specifically, the inulin may be derived from Jerusalem artichoke, dahlia tuber, burdock root, dandelion root, elecampane root, chicory root, or codonopsis. The inulin (or other fructose polymer) may be purified before being used in combination with the personal care products described herein. Alternatively, the inulin (or other fructose polymer) may be used in unpurified form, such as, for example, in an extract obtained from the plant or herb from which the inulin is derived (e.g., Jerusalem artichoke, dahlia tuber, burdock root, dandelion root, elecampane root, chicory root, codonopsis, etc.). It will be recognized by one skilled in the art that when used in unpurified form, such as in extract form, the extract will comprise additional components such as, for example, a solvent.

The fructose polymers may be comprised solely of fructose units, or alternatively, may contain a terminal glucose unit. The fructose polymers may be represented by the general formula $F_n$ or $GF_m$, wherein F represents a fructose unit, G represents a glucose unit, n represents the number of fructose units linked to each other in the carbohydrate chain, and m represents the number of fructose units linked to the terminal glucose unit.

The number of saccharide units (fructose and glucose units) in one fructose polymer, i.e. the values n and m in the above formulas, are commonly referred to as the degree of polymerization. Fructose polymers may vary with regards to their degree of polymerization. For purposes of the present invention, the exact degree of polymerization of the fructose polymer is not critical, but is preferably greater than about 2, more preferably greater than about 10, more preferably greater than about 20, and even more preferably greater than about 30. As the degree of polymerization increases, the coating of the skin typically increases. As one skilled in the art will recognize based on the disclosure herein, as the degree of polymerization increases, so does the viscosity of the formulation. As such, the degree of polymerization is suitably chosen with viscosity of the formulation in mind.

In one specific example, the fructose polymer may be a fructooligosaccharide. It will be appreciated by those skilled in the art that the degree of polymerization of fructans, such as inulin, may vary depending on the source from which they are derived. In addition, fructans derived from a single source may comprise fructose polymers having different degrees of polymerization. For example, inulin may comprise multiple types of fructose polymers having different degrees of polymerization. Thus, in one aspect, the personal care products described herein may comprise more than one type of fructose polymer, each of which has a different degree of polymerization.

Suitable fructose polymers for use in combination with the personal care products described herein include fructose polymers that inhibit the adherence of flora to the surface of skin, mucosa, or inanimate surfaces. Preferably, the fructose polymers inhibit the adherence of flora to the surface of skin, mucosa, or inanimate surfaces by at least about 15%; that is, the fructose polymer reduces by at least about 15% the amount of flora that would otherwise adhere to the skin, mucosa, or inanimate surface in the absence of the fructose polymer. More preferably, the fructose polymers inhibit the adherence of flora to the surface of skin, mucosa, or inanimate surfaces by at least about 25%, more preferably by at least about 40%.

The protocols for testing the ability of fructose polymers to inhibit the adherence of various types of flora to the surface of skin are set forth in the Examples. In general, the ability of fructose polymers to affect the adherence of an organism to skin is determined by comparing the adherence of the organism to skin in the presence of the fructose polymers, to the adherence of the organism to skin in the absence of the fructose polymers. It will be apparent to one skilled in the art that the protocols described herein may be readily modified to test the ability of fructose polymers to inhibit the adherence of a variety of different types of flora, in addition to those tested herein.

The products of the present invention may also comprise a combination of two or more types of fructose polymers described herein. Numerous combinations of fructose polymers may be introduced onto a wipe substrate, absorbent substrate, or into a wet wipe solution for use in combination with a wipe substrate, so as to optimize the anti-adherent effect of the fructose polymers. For example, the fructose polymers used in combination may have different degrees of polymerization, different linkage bonds, and/or different degrees of branching or crosslinking. Such combinations may comprise fructose polymers derived from two different sources, or alternatively, may comprise fructose polymers such as inulin derived from a single source. As will be recognized by one skilled in the art based on the disclosure herein, when preparing the antiadherent formulations described herein, the solubility of the fructose polymer in the formulation must be considered.

In addition to wipes and absorbent articles, the present invention is also directed to a method for inhibiting the adherence of flora to a surface, such as the surface of skin or mucosa, or an inanimate surface. The method includes contacting a wipe, such as a wet or dry wipe, with the surface, the wipe comprising a fibrous sheet material and a formulation; and transferring the formulation to the surface. Preferably, the wipe is a wet or dry wipe described herein. For example, the wet wipe may comprise a liquid fromulation comprising at least about 0.1% (by total weight of the liquid formulation) of a fructose polymer. Additionally, a suitable method includes contacting an absorbent article, such as a diaper, tampon, bath tissue, etc. with the surface, the absorbent article comprising an absorbent substrate and a formulation, and transferring the formulation to the surface. Preferably, the absorbent article is an absorbent article described herein.

When present on a dry substrate, the fructose polymers that inhibit the adherence of flora to the surface (e.g. skin, mucosa, or inanimate surfaces) are preferably present in the formulation in an amount of at least about 0.1% (by total weight of the formulation), more preferably in an amount of at least about 0.5% (by total weight of the formulation), and even more preferably in an amount of at least about 1.0% (by total weight of the formulation). When present as part of the liquid formulation used in combination with a wet wipe or absorbent article, the fructose polymers are preferably present in an amount of at least about 0.1% (by total weight of the liquid formulation), more preferably in an amount of at least about 0.5% (by total weight of the liquid formulation), and even more preferably in an amount of at least about 1.0% (by total weight of the liquid formulation).

Liquid formulations comprising fructose polylmers, described herein, suitable for use in combination with a wipe or absorbent article are generally aqueous solutions, and can be homogeneous solutions, suspensions, emulsions, or structured liquids. A preferred embodiment is an aqueous wet wipe solution. Many of the fructose polymers are substantially water-soluble or can be easily solubilized in water using techniques known to one skilled in the art to provide solutions comprising the fructose polymers. In general, fructose polymers that have a high degree of branching or crosslinking are less soluble than fructose polymers that are a substantially linear chain, and in some cases substantially less soluble. Some fructose polymers described herein which are not substantially water-soluble or easily solubilized can be suspended, emulsified, or introduced into a structured liquid utilizing techniques known to one skilled in the art. Suitable emulsions include oil-in-water emulsions which can be prepared using suitable emulsifiers having an HLB greater than about 7 or can be water-in-oil emulsions prepared using suitable emulsifiers having an HLB of less than about 7. In order to sufficiently protect the water-soluble and/or hydrophilic compounds from premature oxidation during processing and/or product shelf storage, water-in-oil emulsions are typically particularly useful. The emulsified layer around the water phase can prevent oxygen from entering the water phase. As noted above, the fructose polymers may also be suspended in a structured liquid such that they can be easily transferred to the skin.

Alternatively or additionally, the fructose polymers can be encapsulated to prevent premature oxidation during process and product storage. Many encapsulation techniques known in the art can be utilized including those which provide sustained release, triggered release, targeted release or a combination of these release mechanisms. Other release mechanisms known in the art and suitable for use in accordance with the present invention include friction/pressure release, pH related release, water release, water evaporation release, and the like. Encapsulated fructose polymers can be delivered from both wet and dry wipe products. Microencapsulation materials suitable for use in combination with the fructose polymers described herein include those available from Salvona, LLC (Dayton, N.J.).

Additionally, liposomes and/or nanosomes can be utilized to deliver and protect the fructose polymers described herein from premature oxidation in both a wet and a dry wipe product. As used herein, the terms liposomes and nanosomes are meant to include closed vesicles with walls composed of lipid-bilayer membranes to protect and deliver the core compound material.

Another method for delivering fructose polymers from a wet or dry wipe product or absorbent article and protecting these components from premature oxidation includes utilizing polymeric entrapment systems such as microspheres, microsponges, and polytraps such as those available from Advance Polymer Systems (Redwood City, Calif.). The fructose polymers can be entrapped or adsorbed into the interstitial spaces of a polymer matrix thereby protecting the fructose polymers from degredation and/or premature oxidation.

The fructose polymers may be present on a dry wipe in the form of a dry powder. In one embodiment, the dry wipes are contacted with skin where moisture present on the skin wets the dry powder, thus enhancing transfer of the powder to the skin. In another embodiment, the dry wipe is wetted prior to contacting the wipe with the skin.

Particularly useful for delivering the fructose polymers from dry substrates are semi-solid or solid formulations that transfer to the skin during use by the consumer. These formulations can be hydrophobic or hydrophilic in nature. The hydrophobic formulations are semi-solid or solid in nature at room temperature with a melting point greater than about 35° C. and contain from about 5 to about 95 weight percent of an emollient, from about 5 to about 95 weight percent of a solidifying agent such as an alpha olefin polymer, polyethylene, oxidized polyethylene, fatty alcohol, wax, or solid esters with a melting point of 35° C. or greater, from about 1 to about 50 weight percent of a viscosity enhancer such as silica, ethylene vinyl acetate copolymers, or an organo-clay and from about 0.1 to about 15 weight percent of an antioxidant agent.

The hydrophilic formulations are semi-solid or solid at room temperature with a melting point greater than about 35° C. and contain from about 30 to about 90 weight percent of a hydrophilic solvent/emollient such as water, propylene glycol, butylene glycol, low molecular weight (less than about 720) polyethylene glycols, dipropylene glycol glycerin, silicone glycols, methyl propanediol, or pentylene glycol, from about 10 to about 50 weight percent high molecular weight (greater than about 750) polyethylene glycol, from about 5 to about 40 weight percent of a fatty alcohol having from about 14 to about 30 carbons in the chain, optionally from about 1 to about 15 weight percent of a viscosity enhancer such as clays, glyceryl polyacrylates, or glyceryl polymethacrylates and from about 0.1 to about 15 weight percent of an antioxidant agent.

The dry wipe formulations can also be readily emulsifiable solid formulations with a melting point greater than about 35° C. and contain from about 5 to about 95 weight percent of a hydrophobic or hydrophilic emollient as set forth above, from about 5 to about 95 weight percent of a suitable solidifying agent as set forth above, from about 5 to about 25 weight percent of a suitable emulsifier and from about 1 to about 15 weight percent of an antioxidant agent. The suitable emulsifier can be anionic, cationic, amphoteric, zwitterionic, or nonioinic and combinations thereof.

In order to enhance consumer appeal, additional ingredients can be added to the above-described formulations. Suitable additional ingredients include, for example, anti-acne actives, antifoaming agents, antimicrobial actives, antifungal actives, antiseptic actives, antioxidants which prevent oxidation during processing and storage by preferentially oxidizing, astringents, colorants, deodorants, film formers, fragrances, moisturizers, skin protectants, sunscreen actives, and solvents.

The present invention is illustrated by the following examples which are merely for the purpose of illustration and are not to be regarded as limiting the scope of the invention or manner in which it may be practiced.

EXAMPLES

Example 1

Inhibition of *P. aeruginosa* Attachment to VITRO-SKIN® Substrate with Inulin

Inulin was shown to inhibit the attachment of *Pseudomonas aeruginosa* to VITRO-SKIN® synthetic skin substrate. The protocol described herein can also be applied to test the effect of inulin and other fructose polymers on the adhesion of other bacteria, yeast, or fungi to the skin.

Two days prior to the test a bacterial culture was started by inoculating 10 ml Luria-Bertani (LB) (Sigma-Aldrich, St. Louis, Mo.) with one frozen bead of *Pseudomonas aeruginosa* (ATCC # 27853), and incubating the culture overnight at 37° C. with agitation at 125 rpm.

One day prior to the test a 100 ml LB culture was inoculated with 100 µl of the overnight culture and grown overnight at 37° C. with agitation at 125 rpm. VITRO-SKIN® synthetic skin substrate (N19, IMS, Milford, Conn.) was cut with a #2 size boring tool and placed into the wells of a 96 well tissue culture plate (Costar #3596, Corning Inc., Corning, NY). The plates were kept in a humidity chamber overnight until use to prevent dehydration of the tissues.

The day of the test, the optical density at 650 nm (OD) of the overnight culture was measured using a Spectramax spectrophotometer (Molecular Devices, Sunnyvale, Calif.). The culture was centrifuged at 4,500×g for 10 minutes at 4° C. (J-251 centrifuge, Beckman, Fullerton, Calif.) to pellet the bacteria. The bacteria were resuspended in phosphate buffered saline (PBS) to give a concentration of $2 \times 10^{10}$ cells/ml (1 OD equals $1 \times 10^9$ cells/ml).

A 20% (w/v) solution of each inulin source (Chicory root, Dahlia tuber from Sigma-Aldrich, St. Louis, Mo.) was prepared by mixing 0.3 g inulin with PBS (Invitrogen, Carlsbad, Calif.) to a final volume of 1.5 ml. Tween 20 (Sigma-Aldrich, St. Louis, Mo.) was included as a positive control, and a 4% (v/v) stock was prepared by mixing 40 µl of Tween 20 to 960 µl PBS. The Tween 20 stock was diluted to prepare a 2% (v/v) solution of Tween 20 by mixing 800 µl of the 4% solution and 800 µl of PBS. A two fold dilution series was prepared for each inulin source as follows:

10%: 800 µl of the 20% solution plus 800 µl of PBS
5%: 800 µl of the 10% solution plus 800 µl of PBS
2.5%: 800 µl of the 5% solution plus 800 µl of PBS
1.25% 800 µl of the 2.5% solution plus 800 µl of PBS.
All tests were run five times (n=5).

For the applied dose, 50 µl of each inulin dilution, Tween 20 alone, or PBS alone was added to the VITRO-SKIN® discs followed immediately by 50 µl of either the bacteria cells or PBS. Samples containing 50 µl inulin dilutions and 50 µl PBS served as a background controls for the inulin samples. Samples containing 50 µl Tween 20 and 50 µl PBS served as background controls for the Tween 20 samples. Background controls for the PBS were 100 µl PBS. The plates were gently shaken at room temperature for three hours. The tissues were washed three times with 250 µl of PBS, and transferred to an opaque white 96 well plate (Costar # 3922). 200 µl of AlamarBlue™ (Trek Diagnostic Systems, Cleveland, Ohio) in LB (20 µl AlamarBlue™+180 µl LB per well) was added to each well. AlamarBlue™ conversion was monitored every 15 minutes in a microfluorometer (Fluoroskan Ascent, Thermo-Labsystems, Beverly, Mass.) for 120 minutes with an excitation of 544 nm and emission of 590 nm. In between readings the plates were covered and incubated at 37° C.

Results are expressed as percent bacteria adhered to the tissue relative to the PBS control. The percentage is based on the number of cells that adhered to the skin in the inulin-containing (or Tween 20-containing control) samples as compared to the number of cells that adhered to the skin in the PBS control (i.e. PBS plus bacteria cells), as determined by the AlamarBlue® levels (relative fluorescence units (RFU)) at 120 minutes. The percent adherence was calculated by the formula:

(RFU of the sample–RFU of appropriate background control)/(average of the RFU of the PBS treatment–average RFU of PBS background control)*100.

The results for the five wells for each dilution step were averaged, and the percent attached as compared to the PBS control treatment was calculated.

The results are given in Tables 1 and 2. The results, as shown in Table 1, indicate that inulin has the ability to interfere with the attachment of *P. aeruginosa* to VITRO-SKIN® substrate. The effect appears to be dose dependent (i.e. there was an increase in efficacy of inhibition with increasing dose of inulin) and is not affected by the source of inulin. Table 2 shows a statistical comparison between the effectiveness of the PBS, chicory root, dahlia tuber, and Tween 20 treatments at various concentrations. The letters A-F indicate treatments for which the percent attachment was not statistically different. For example, the PBS, chicory root (1.25%), and dahlia tuber (1.25%) treatments (labeled "A") produced results that were not statistically different. Likewise, the chicory root (1.25% and 2.5%), and dahlia tuber (1.25% and 2.5%) treatments (labeled "B") produced results that are not statistically different. However, the chicory root (2.5%) and dahlia tuber (2.5%) treatments (labeled "B" but not "A") produced results that are statistically different from the results produced by the PBS treatment (labeled "A" only).

TABLE 1

Inulin Blocks Attachment of *P. aeruginosa*

| Treatment | Treatment Concentration (%) | % Attached as Compared to PBS Treatment | STDEV |
|---|---|---|---|
| PBS | | 100 | 13 |
| Chicory root | 10 | 17 | 19 |
| Chicory root | 5 | 45 | 34 |
| Chicory root | 2.5 | 60 | 27 |
| Chicory root | 1.25 | 92 | 51 |
| Dahlia tuber | 10 | 29 | 33 |
| Dahlia tuber | 5 | 48 | 34 |
| Dahlia tuber | 2.5 | 59 | 31 |
| Dahlia tuber | 1.25 | 86 | 18 |
| Tween 20 | 2 | 50 | 24 | n = 5

TABLE 2

Inulin Blocks Attachment of *P. aeruginosa*.
Statistical Comparisons

| Treatment | Treatment Concentration (%) | Statistical Grouping (Student T, p < 0.05) | | | | |
|---|---|---|---|---|---|---|
| PBS | | A | | | | |
| Chicory root | 1.25 | A | B | | | |
| Dahlia tuber | 1.25 | A | B | C | | |
| Chicory root | 2.5 | | B | C | D | E |
| Dahlia tuber | 2.5 | | B | C | D | E |
| Tween | 2 | | | C | D | E | F |
| Dahlia tuber | 5 | | | C | D | E | F |
| Chicory root | 5 | | | | D | E | F |
| Dahlia tuber | 10 | | | | | E | F |
| Chicory root | 10 | | | | | | F |

Example 2

Inhibition of *P. aeruginosa* Attachment to VITRO-SKIN® Substrate and Porcine Skin with Inulin Inulin was shown to inhibit the attachment of *Pseudomonas aeruginosa* to VITRO-SKIN® synthetic skin substrate and porcine skin. The protocol described herein can also be applied to test the effect of inulin and other fructose polymers on the adhesion of other bacteria, yeast, or fungi to the skin.

Two days prior to the test a bacterial culture was started by inoculating 10 ml of Luria-Bertani (LB) medium with one frozen bead containing *Pseudomonas aeruginosa* (Dr. G. O'Toole, Dept. Microbiol. Dartmouth Medical School, Hanover, N.H.), and incubating the culture overnight at 37° C. with agitation at 125 rpm.

One day prior to the test a 100 ml LB culture was inoculated with 100 µl of the overnight culture and grown overnight at 37° C. with agitation at 125 rpm.

The day of the test the optical density (OD) of the overnight culture was measured at 650 nm using a Spectramax spectrophotometer (Molecular Devices, Sunnyvale, Calif.). The culture was centrifuged at 4,500×g for 10 minutes at 4° C. to pellet the bacteria. The bacteria were resuspended in phosphate buffered saline (PBS) to give a concentration of $2\times10^{10}$ cells/ml (1 OD equals $1\times10^9$ cells/ml). Vitro Skin™ (N19, IMS) synthetic skin substrate, or porcine skin (Buckshire Corp., 2025 N Ridge Rd. Perkasie, Pa.) was cut with a #2 size boring tool and placed into the wells of a 96 well tissue culture plate. The plates were kept in a humidity chamber until use to prevent dehydration of the tissues.

A 20% (w/v) solution of inulin (Jerusalem Artichoke, Sigma Chemical St Louis Mo.) was prepared by mixing 0.3 g inulin with PBS to a final volume of 1.5 ml. This solution was diluted to prepare a 10% inulin solution by mixing 800 µl of the 20% solution plus 800 µl of PBS. A 4% (v/v) of Tween 20 was used as a positive control and was prepared by mixing 60 µl of Tween 20 with 1440 µl PBS. This solution was diluted to prepare a 2% Tween 20 solution by mixing 800 µl of the 4% solution with 800 µl PBS. All experiments were done in triplicate.

The tissues were treated with 50 µl of inulin, Tween 20 alone, or PBS alone followed immediately by 50 µl of either the bacteria cells or PBS. Samples containing 50 µl inulin and 50 µl PBS or samples containing 50 µl Tween 20 and 50 µl PBS served as a background controls for inulin or Tween 20 samples respectively. Background controls for the PBS were 100 µl PBS. The plates were gently shaken at room temperature for three hours. The tissues were washed twice with 250 µl of PBS, and transferred to an opaque white 96 well plate. 200 µl of AlamarBlue™ in LB (20 µl AlamarBlue™+180 µl LB per well) was added to each well. AlamarBlue™ conversion was monitored kinetically in a microfluorometer (Fluoroskan Ascent, Thermo-Labsystems, Beverly, Mass.) for 60 minutes at 37° C., with an excitation of 544 nm and emission of 590 nm.

Results are expressed as percent bacteria adhered to the tissue relative to the PBS control. The percentage is based on the number of cells that adhered to the skin in the inulin-containing (or Tween 20-containing control) samples as compared to the number of cells that adhered to the skin in the PBS control (i.e. PBS plus bacteria cells), as determined by the AlamarBlue® levels (RFU) at 60 minutes. The percent adherence was calculated by the formula:

($RFU$ of the sample–$RFU$ of appropriate background control)/(average of the $RFU$ of the $PBS$ treatment–average $RFU$ of $PBS$ background control)*100.

The results for the three wells comprising each dilution were averaged, and the percent attached as compared to the PBS control treatment was calculated.

The results are given in Tables 3 and 4. The results, as shown in Table 3, indicate that Jerusalem artichoke inulin also inhibited attachment of *P. aeruginosa* to VITRO-SKIN®substrate. It was also observed that the effect of inulin was not unique to a skin simulant (VITRO-SKIN®) but also occurred on porcine skin (Table 4).

TABLE 3

Jerusalem Artichoke Inulin Blocks Attachment of *P. aeruginosa* to VITRO-SKIN ®

| Treatment | Treatment Concentration (%) | % Attached as Compared to PBS Treatment | STDEV |
|---|---|---|---|
| PBS | | 100 | 16 |
| Jerusalem Artichoke | 10 | 53 | 2 |
| Tween 20 | 2 | 10 | 2 | n = 3

TABLE 4

Jerusalem Artichoke Inulin Blocks Attachment of *P. aeruginosa* to Porcine Skin

| Treatment | Treatment concentration (%) | % Attached as compared to PBS Treatment | STDEV |
|---|---|---|---|
| PBS | | 100 | 23 |
| Jerusalem Artichoke | 10 | 25 | 16 |
| Tween 20 | 2 | 70 | 22 | n = 3

Example 3

Inhibition of *P. aeruginosa* Attachment to a Skin Culture by Inulin

The effect of inulin on the attachment of *Pseudomonas aeruginosa* to the EpiDerm™ skin model was tested. The protocol described herein can also be appied to test the effect of inulin and other fructose polymers on the attachment of other bacteria, yeast, and fungi to the skin.

The EpiDerm™ (MatTek, Ashland, Mass.) experiment was performed as outlined by the protocol supplied by the manufacturer for the EPI-200 EpiDerm™.

Two days prior to the test bacterial culture was started by inoculating 10 ml of Luria-Bertani broth (LB) with one to two well isolated colonies of *Pseudomonas aeruginosa* (Dr. G. O'Toole, Dept. Microbiol. Dartmouth Medical School, Hanover, N.H.) and incubating the culture overnight at 37° C. with agitation at 125 rpm.

One day prior to the test a 50 ml LB culture was inoculated with 50 µl of the overnight culture and grown overnight at 37° C. with agitation at 125 rpm. The optical density (at 650 nm) of the overnight culture was measured using a Spectramax spectrophotometer (molecular Devices, Sunnyvale, Calif.). The culture was centrifuged at 4,500×g for 10 minutes at 4° C. to pellet the bacteria. The bacteria were resuspended in phosphate buffered saline (PBS) to give a concentration of $2 \times 10^{10}$ cells/ml (1 OD equals $1 \times 10^9$ cells/ml).

A 20% (w/v) stock of inulin (Jerusalem Artichoke, Sigma Chemical St Louis Mo.) was prepared by mixing 0.20 g of inulin with a sufficient amount of PBS to yield a final volume of 1 ml. This solution was diluted to prepare a 10% inulin solution by mixing 800 µl of the 20% stock plus 800 µl of PBS. Tween 20 was used as a positive control, and a 4% (v/v) stock was prepared by mixing 40 µl of Tween 20 with 960 µl PBS. This solution was diluted to prepare a 2% Tween 20 solution by mixing 800 µl of the 4% solution with 800 µl of PBS. All experiments were repeated twice.

For the applied dose, 50 µl of 20% inulin in PBS, 4% Tween 20 alone, or PBS alone was applied to the EpiDerm™ tissue followed immediately by 50 µl of either the bacteria cells or PBS. Samples containing 50 µl inulin and 50 µl PBS served as background controls for the inulin samples. Samples containing 50 µl Tween 20 and 50 µl PBS served as background controls for the Tween 20 samples. Background controls for the PBS were 100 µl PBS. The tissues were incubated at 37° C., 5% $CO_2$ for three hours to allow the bacteria to adhere. After three hours, the tissue was analyzed for the number of adhered bacteria.

To measure adherence of *P. aeruginosa* to the EPI-DERM™ tissue, the liquid remaining on the tissue was first transferred to a fresh microcentrifuge tube. The tissues were washed twice with 200 µl PBS, and the washes were pooled with the liquid from above and saved to determine the amount of bacteria that did not bind (unbound samples). The tissues (bound samples) were then transferred to a clean tube and frozen at –70° C. for at least 15 minutes. The unbound samples were centrifuged at 5,000 rpm for 10 minutes in an Eppendorf 5415C microcentrifuge (Brinkmann Instruments, Westbury, N.Y.) to pellet the bacteria cells. The supernatant was carefully aspirated and the unbound samples were frozen at –70° C. for at least 15 minutes. The unbound and bound samples were thawed and resuspended in 150 µl of B-PER II Bacterial protein extraction reagent (Pierce # 78260, Rockford, Ill.). The samples were then vortexed for 10 min at a low setting, followed by centrifugation at 13,000 rpm for five minutes in the microcentrifuge. 100 µl of the bound cleared lysate or 10 µl of the unbound cleared lysate plus 90 µl B-PER reagent was added to wells in a white opaque 96 well plate (Costar # 3922, Corning Incorporated, Corning, N.Y.). Fluorescence was monitored in a microfluorometer at an excitation of 485 nm and an emission of 510 nm.

Results are expressed as percent bacteria adhered to the tissue relative to the PBS control. The percentage is based on the number of cells that adhered to the tissue in the inulin-containing (or Tween 20-containing control) samples as compared to the number of cells that adhered to the tissues in the PBS control (i.e. PBS plus bacteria cells). The percent adherence was calculated by the formula:

(RFU in bound fraction of the inulin or Tween 20 sample−average background RFU)/(average of the RFU in the bound fraction of the cells alone treatment−average background RFU)*100.

The results for the two tests for inulin or Tween 20 were averaged, and the percent attached as compared to the PBS control treatment was calculated.

The results are given in Table 5. The results indicate that Jerusalem artichoke inulin inhibited attachment of *Pseudomonas aeruginosa* to EpiDerm™, further confirming that inulin can inhibit attachment of bacteria to skin.

TABLE 5

Jerusalem Artichoke Inulin Blocks Attachment of *P. aeruginosa* to EpiDerm™

| Treatment | Treatment Concentration (%) | % Attached as Compared to PBS Treatment |
|---|---|---|
| PBS |  | 100 |
| Inulin | 10 | 57 |
| Tween 20 | 2 | 73 | n = 2

In view of the above, it will be seen that the several objects of the invention are achieved. As various changes could be made in the above-described products and methods without departing from the scope of the invention, it is intended that all matter contained in the above description be interpreted as illustrative and not in a limiting sense.

What is claimed is:

1. A wet wipe comprising a fibrous sheet material and a liquid formulation, the liquid formulation comprising at least about 0.1% by total weight of the liquid formulation of a fructose polymer, wherein the fructose polymer is selected from the group consisting of inulin, levan, and graminan, wherein the fructose polymer is encapsulated, and wherein the fructose polymer has a degree of polymerization of at least about 10.

2. The wet wipe as set forth in claim 1 wherein the fructose polymer is inulin.

3. The wet wipe as set forth in claim 1 wherein the fructose polymer is derived from a plant of the Composite family.

4. A wet wipe comprising a fibrous sheet material and a liquid formulation, the liquid formulation comprising at least about 0.1% by total weight of the liquid formulation of a fructose polymer, wherein the fructose polymer is selected from the group consisting of inulin, levan, and graminan, wherein the fructose polymer is encapsulated, and wherein the fructose polymer is contained in an extract derived from a plant selected from the group consisting of Jerusalem artichoke, dahlia tuber, burdock root, dandelion root, elecampane root, chicory root, and codonopsis.

5. The wet wipe as set forth in claim 1 wherein the fructose polymer has a degree of polymerization of at least about 20.

6. The wet wipe as set forth in claim 5 wherein the fructose polymer has a degree of polymerization of at least about 30.

7. The wet wipe as set forth in claim 1 wherein the liquid formulation comprises an emulsified fructose polymer.

8. The wet wipe as set forth in claim 1 wherein the liquid formulation is a structured liquid.

9. The wet wipe as set forth in claim 1 wherein the liquid formulation is a suspension comprising the fructose polymer.

10. The wet wipe as set forth in claim 1 wherein the fructose polymer is present in an amount of at least about 0.5% by total weight of the liquid formulation.

11. The wet wipe as set forth in claim 1 wherein the fructose polymer is present in an amount of at least about 1.0% by total weight of the liquid formulation.

* * * * *